United States Patent
Golz et al.

(10) Patent No.: US 7,297,483 B2
(45) Date of Patent: Nov. 20, 2007

(54) ISOLATED LUCIFERASES AND THE USE THEREOF

(75) Inventors: Stefan Golz, Essen (DE); Bernd Kalthof, Wuppertal (DE); Svetlana Markova, Krasnoyarsk (RU); Ludmila Frank, Krasnoyarsk (RU); Eugene Vysotski, Krasnoyarsk (RU)

(73) Assignee: Bayer Aktiengesellschaft, D 51368 Leverkusen (DE)

( * ) Notice: Subject to any disclaimer, the term of this patent is extended or adjusted under 35 U.S.C. 154(b) by 288 days.

(21) Appl. No.: 10/416,752

(22) PCT Filed: Nov. 22, 2001

(86) PCT No.: PCT/EP01/13597

§ 371 (c)(1),
(2), (4) Date: Oct. 1, 2003

(87) PCT Pub. No.: WO02/42470

PCT Pub. Date: May 30, 2002

(65) Prior Publication Data

US 2004/0219527 A1 Nov. 4, 2004

(30) Foreign Application Priority Data

Nov. 23, 2000 (DE) .............................. 100 58 091

(51) Int. Cl.
  *C12Q 1/68* (2006.01)
(52) U.S. Cl. ........................................... 435/6
(58) Field of Classification Search ..................... None
  See application file for complete search history.

(56) References Cited

U.S. PATENT DOCUMENTS 5,604,123 A 2/1997 Kazami et al. ............. 435/189

FOREIGN PATENT DOCUMENTS

WO 9949019 9/1999
WO WO9949019 * 9/1999

OTHER PUBLICATIONS

Thomson, C.M., Herring, P.J., and Campbell, A.K.; "The Widespread Occurrence and Tissue Distribution of the *Imidazolopyrazine luciferins*", J. Biolumin Chemilumin, 12: 87-91 (1997).
Campbell, A.K., and Herring, P.J.; "*Imidazolopyrazine bioluminescence* in copepods and other marine organisms", Marine Biology, 104: 219-225 (1990).
Inouye, S., Watanabe, K., Nakamura, H., and Shimomura, O.; "Secretational luciferase of the luminous shrimp *Oplophorus gracilirostris* : cDNA cloning of a novel *Imidazopyrazinone luciferase*", FEBS Letters, 481: 19-25 (2000).
Inouye, S., Ohmiya, Y., Toya, Y., and Tsuji, F. I., "Imaging of liciferase secretion from transformed Chinese hamster ovary cells", *Proc. Natl. Acad. Sci. USA*, 89: 9584-9587 (1992).
Hastings, J. W.; "Chemistries and colors of bioluminescent reactions: a review", Gene, 173: 5-11 (1996).

* cited by examiner

*Primary Examiner*—Teresa E. Strzelecka
*Assistant Examiner*—Heather Calamita (57) ABSTRACT

This invention relates to an isolated nucleic acid molecule which is a) a nucleic acid molecule comprising SEQ ID No. 3, or b) a nucleic acid molecule which exhibits at least 90% sequence identity to the nucleic acid molecule of SEQ ID No. 3, and the claimed nucleic acid molecule encodes luciferase. It also relates to an expression vector and to a transformed host cell.

4 Claims, 7 Drawing Sheets

Figure 1:
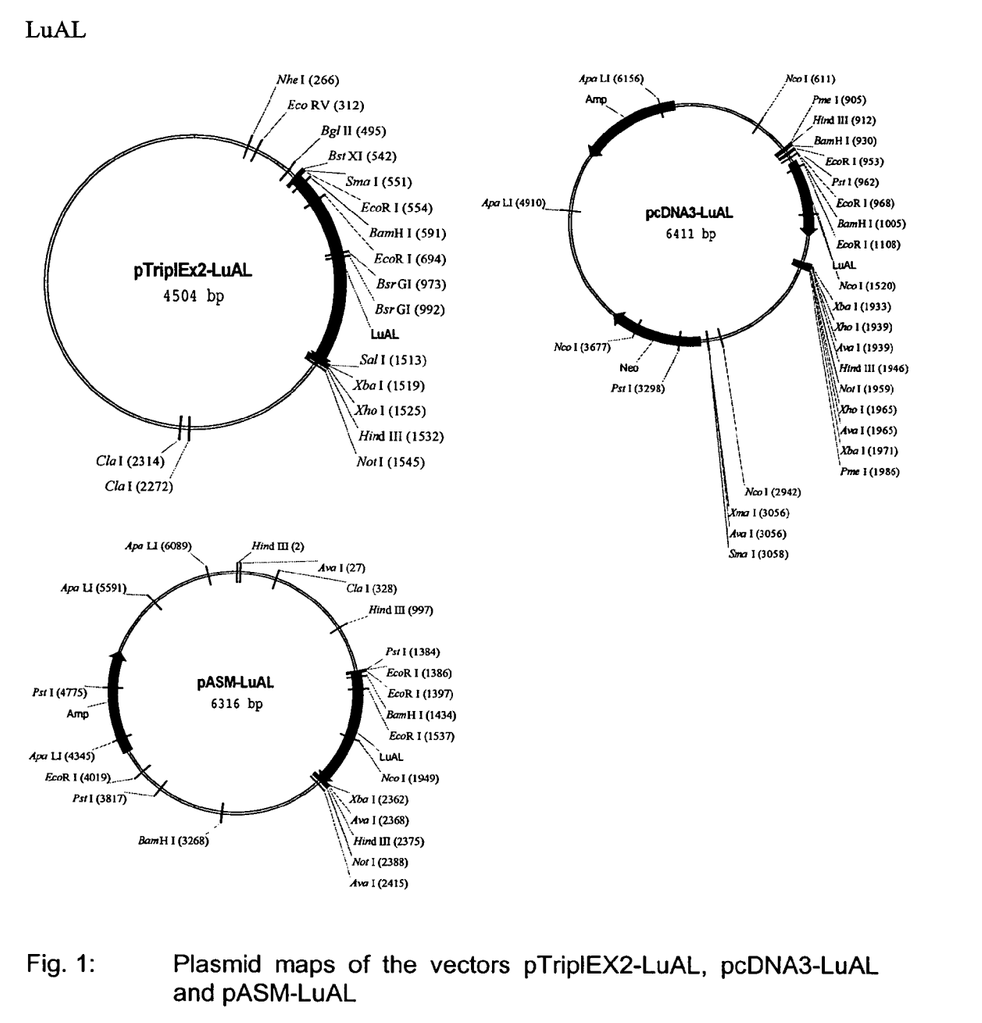

Fig. 1: Plasmid maps of the vectors pTriplEX2-LuAL, pcDNA3-LuAL and pASM-LuAL

Figure 2:
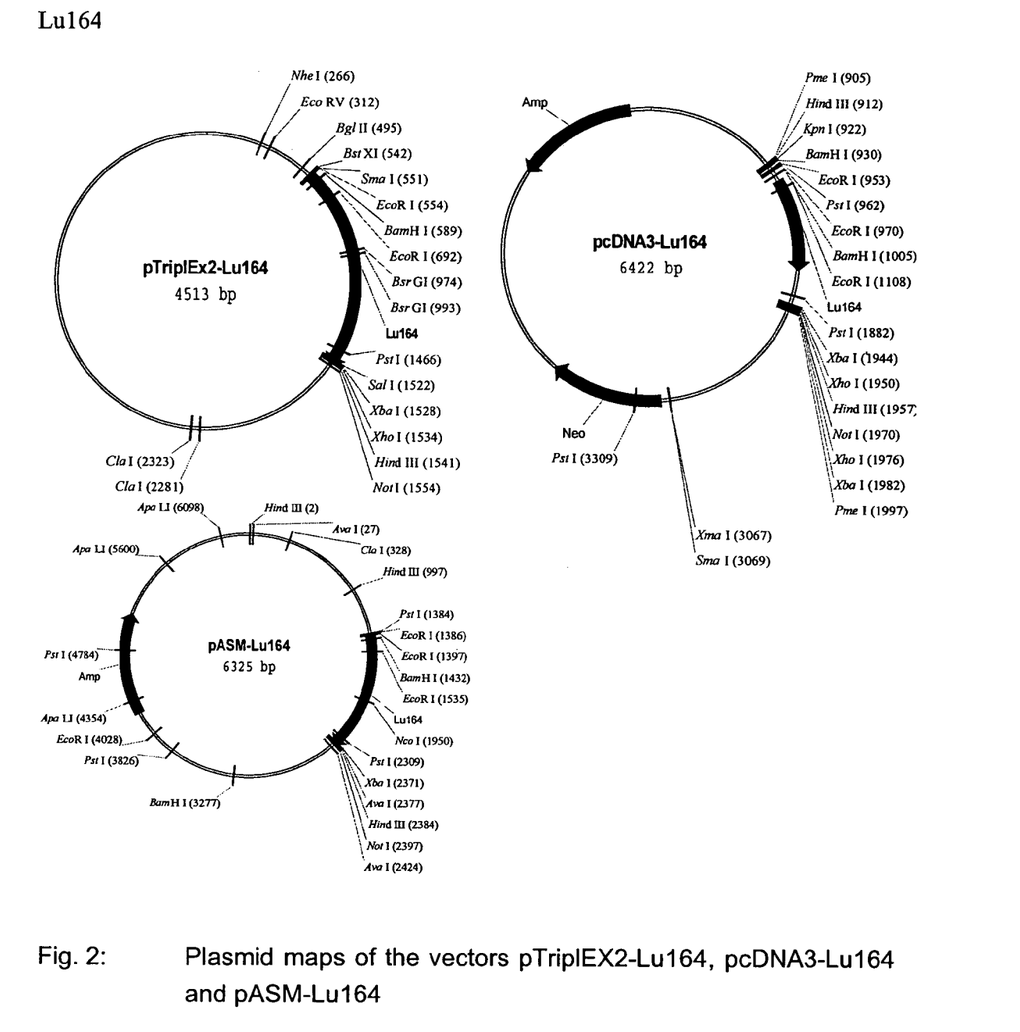

Fig. 2: Plasmid maps of the vectors pTriplEX2-Lu164, pcDNA3-Lu164 and pASM-Lu164

Lu22

Figure 3:
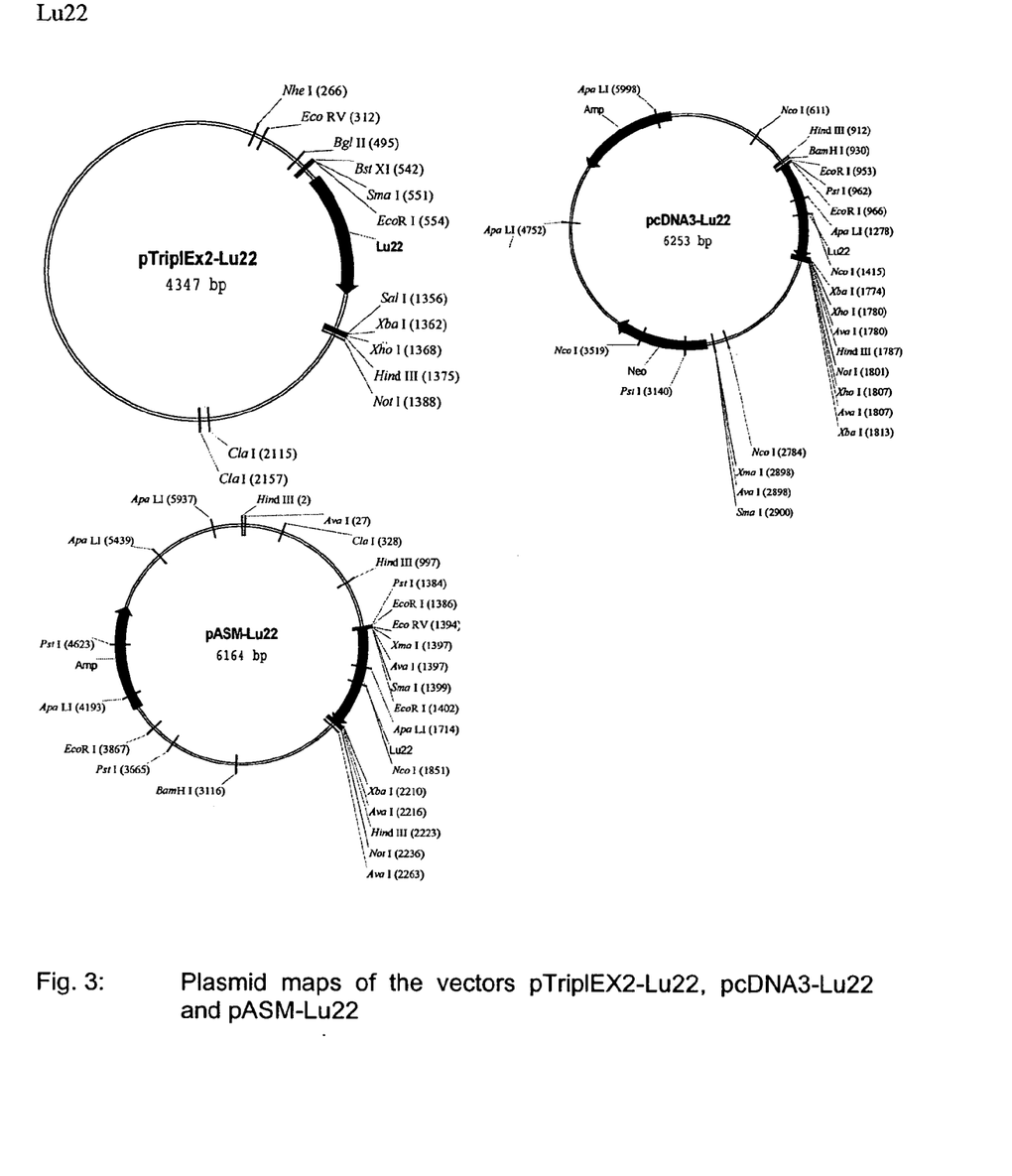

Fig. 3: Plasmid maps of the vectors pTriplEX2-Lu22, pcDNA3-Lu22 and pASM-Lu22

Figure 4:
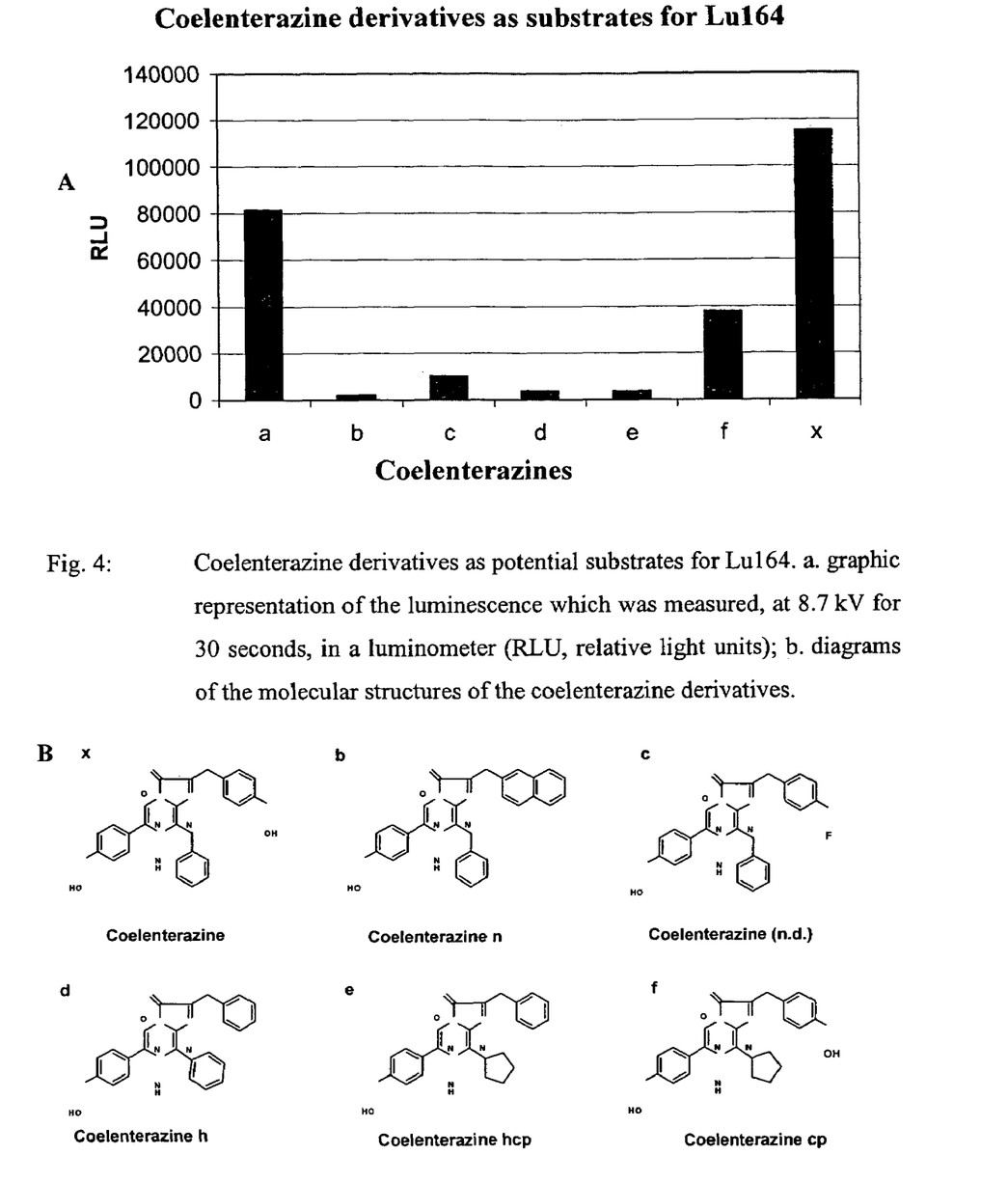

Fig. 4: Coelenterazine derivatives as potential substrates for Lu164. a. graphic representation of the luminescence which was measured, at 8.7 kV for 30 seconds, in a luminometer (RLU, relative light units); b. diagrams of the molecular structures of the coelenterazine derivatives.

A

B

C

Figure 5:
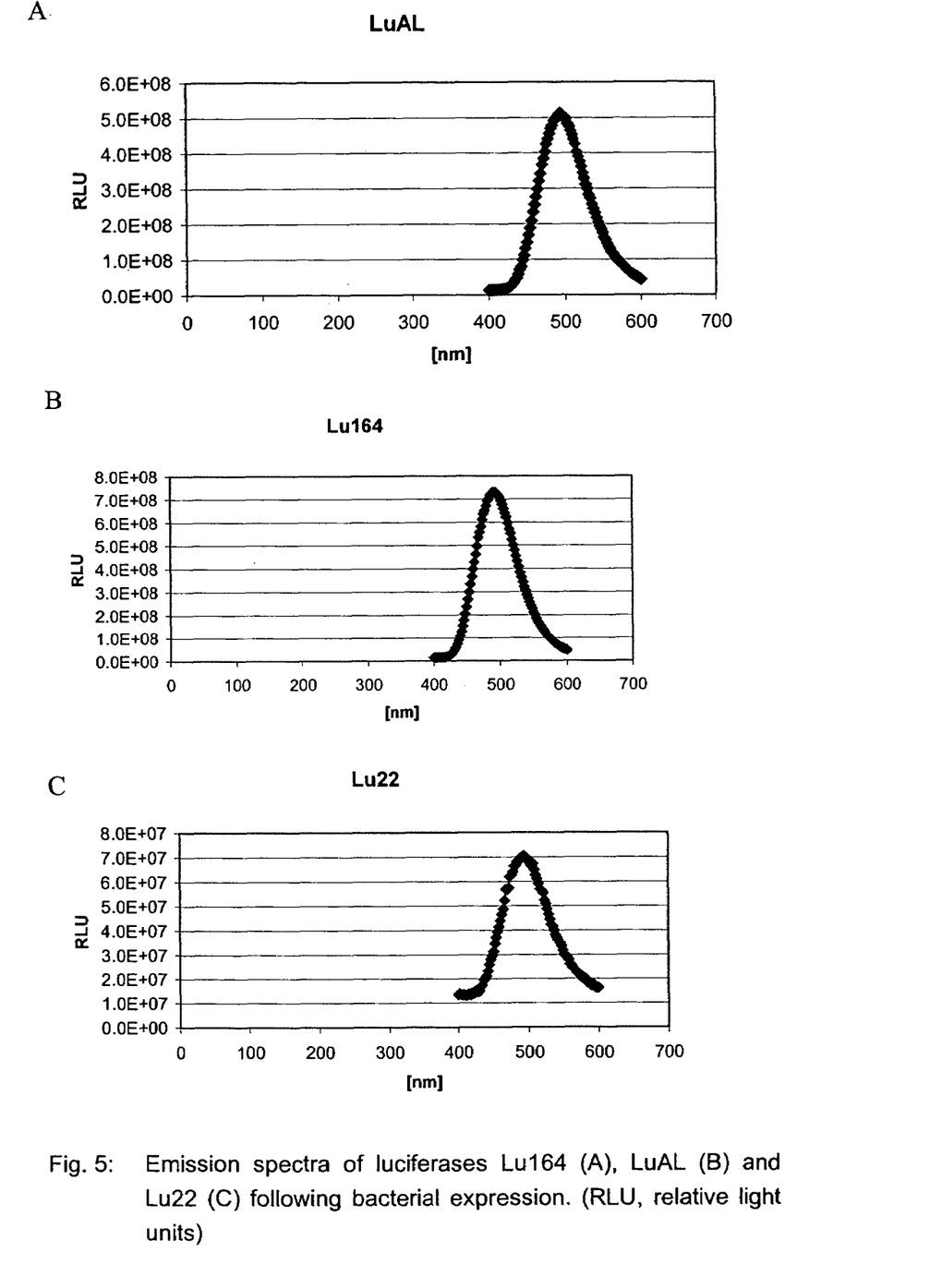

Fig. 5: Emission spectra of luciferases Lu164 (A), LuAL (B) and Lu22 (C) following bacterial expression. (RLU, relative light units)

Figure 6:
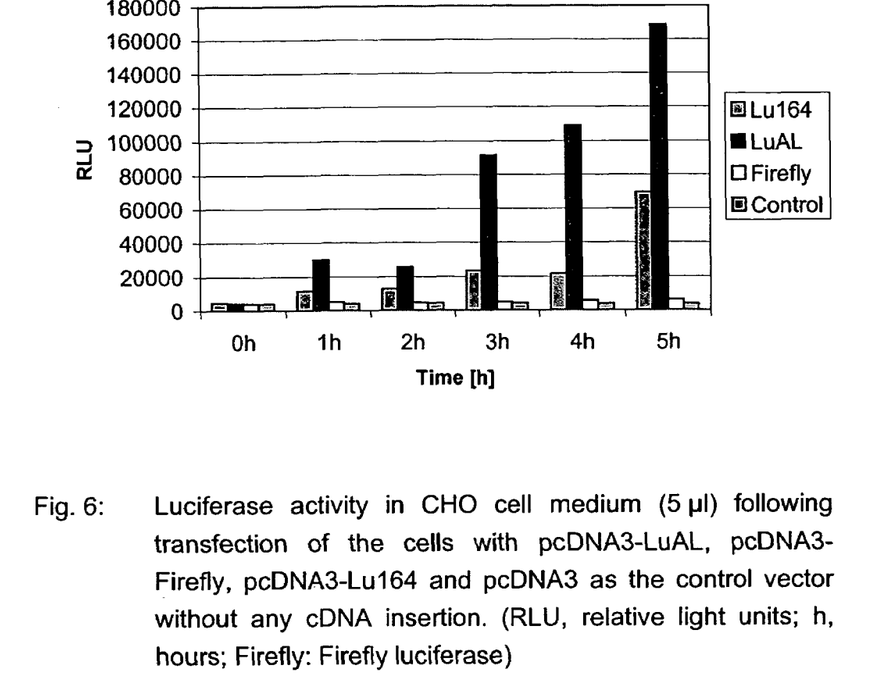

Fig. 6: Luciferase activity in CHO cell medium (5 µl) following transfection of the cells with pcDNA3-LuAL, pcDNA3-Firefly, pcDNA3-Lu164 and pcDNA3 as the control vector without any cDNA insertion. (RLU, relative light units; h, hours; Firefly: Firefly luciferase)

Figure 7:
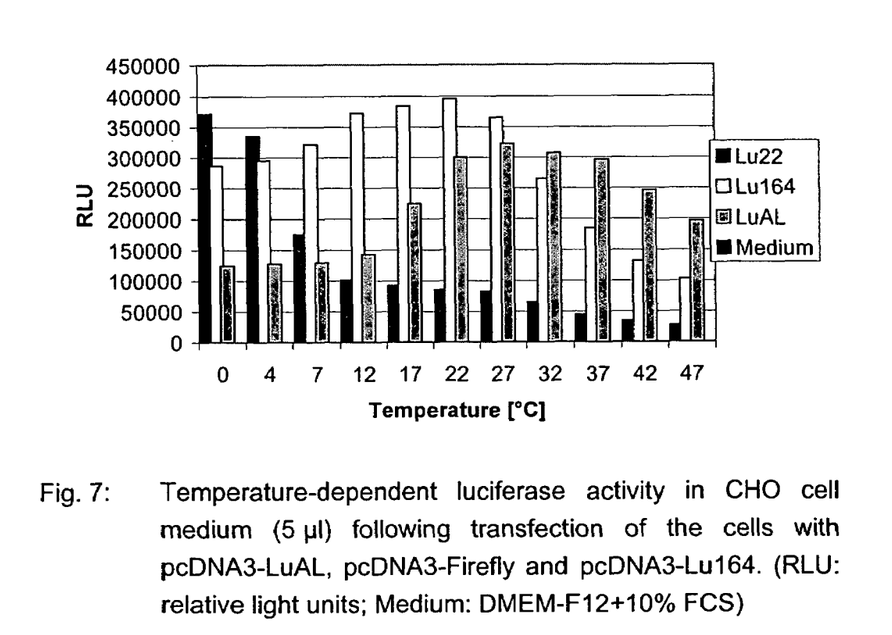

Fig. 7: Temperature-dependent luciferase activity in CHO cell medium (5 µl) following transfection of the cells with pcDNA3-LuAL, pcDNA3-Firefly and pcDNA3-Lu164. (RLU: relative light units; Medium: DMEM-F12+10% FCS)

Figure 8:
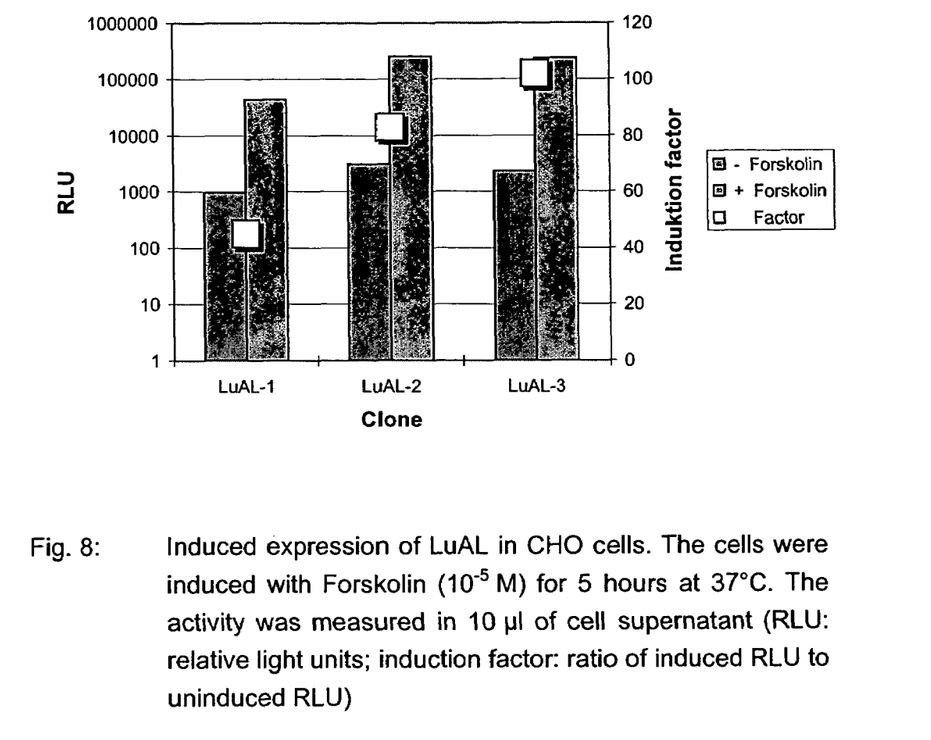

Fig. 8: Induced expression of LuAL in CHO cells. The cells were induced with Forskolin ($10^{-5}$ M) for 5 hours at 37°C. The activity was measured in 10 µl of cell supernatant (RLU: relative light units; induction factor: ratio of induced RLU to uninduced RLU)

Figure 9:
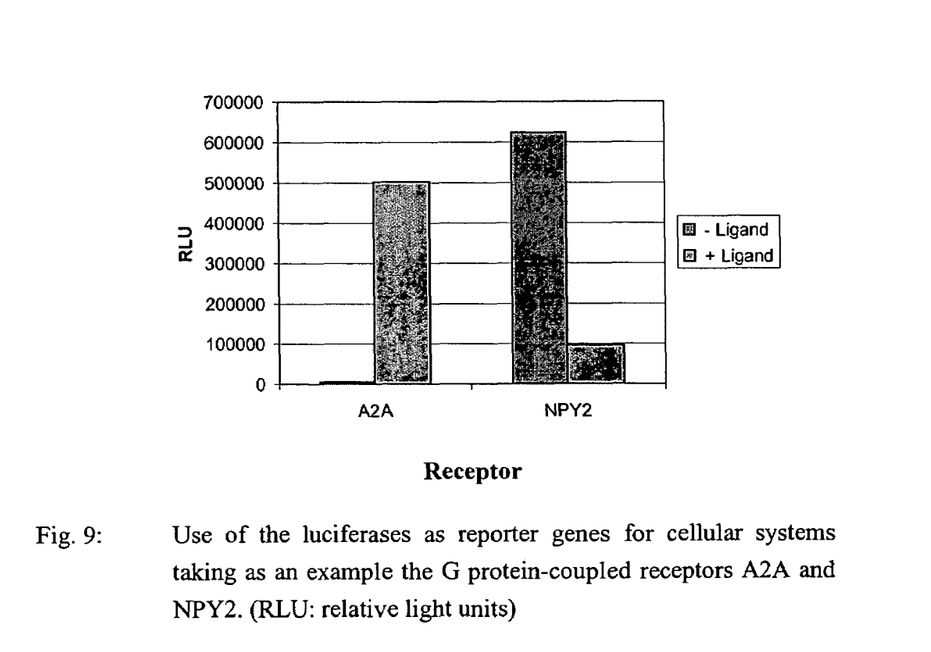

Fig. 9: Use of the luciferases as reporter genes for cellular systems taking as an example the G protein-coupled receptors A2A and NPY2. (RLU: relative light units)

SEQUENCE LISTING

```
<160> NUMBER OF SEQ ID NOS: 6

<210> SEQ ID NO 1
<211> LENGTH: 657
<212> TYPE: DNA
<213> ORGANISM: Metridia longa

<400> SEQUENCE: 1
atggatatga gggttatctt tgctcttgtt ttctcatcat tggttcaggc caaatcaact    60
```

```
gaattcgatc ctaacattaa cattgttggt ttagaaggaa aatttggtat aacaaacctt     120
gagacggatt tattcacaat atgggagaca atggatgtca tcaaatcaga tattacagat     180
actgatagag tcagcaactt tgttgcaact gaaaccgatg ctaaccgtgg gaaaatgcct     240
ggcaaaaaac tgccactggc agttatcatg gaaatggaag ccaatgcttt caaagctggc     300
tgcaccaggg gatgccttat ctgtctttca aaataaagt gtacagccaa atgaaggtg       360 tacattccag gaagatgtca tgattatggt ggtgacaaga aaactggaca ggcaggaata     420
gttggtgcaa ttgttgacat tcccgaaatc tctggattta aggagatggc acccatggaa     480
cagttcattg ctcaagttga tctttgcgct acctgcacta ctggatgtct caaaggtctt     540
gccaatgtta agtgctctga actcctgaag aaatggctgc ctggcagatg tgcaagtttt     600
gctgacaaga ttcaaaaaga agttcacaat atcaaaggca tggctggaga tcgttga       657
```

<210> SEQ ID NO 2
<211> LENGTH: 218
<212> TYPE: PRT
<213> ORGANISM: Metridia longa

<400> SEQUENCE: 2

```
Met Asp Met Arg Val Ile Phe Ala Leu Val Phe Ser Ser Leu Val Gln
1               5                   10                  15

Ala Lys Ser Thr Glu Phe Asp Pro Asn Ile Asn Ile Val Gly Leu Glu
            20                  25                  30

Gly Lys Phe Gly Ile Thr Asn Leu Glu Thr Asp Leu Phe Thr Ile Trp
        35                  40                  45

Glu Thr Met Asp Val Ile Lys Ser Asp Ile Thr Asp Thr Asp Arg Val
    50                  55                  60

Ser Asn Phe Val Ala Thr Glu Thr Asp Ala Asn Arg Gly Lys Met Pro
65                  70                  75                  80

Gly Lys Lys Leu Pro Leu Ala Val Ile Met Glu Met Glu Ala Asn Ala
                85                  90                  95

Phe Lys Ala Gly Cys Thr Arg Gly Cys Leu Ile Cys Leu Ser Lys Ile
            100                 105                 110

Lys Cys Thr Ala Lys Met Lys Val Tyr Ile Pro Gly Arg Cys His Asp
        115                 120                 125

Tyr Gly Gly Asp Lys Lys Thr Gly Gln Ala Gly Ile Val Gly Ala Ile
    130                 135                 140

Val Asp Ile Pro Glu Ile Ser Gly Phe Lys Glu Met Ala Pro Met Glu
145                 150                 155                 160

Gln Phe Ile Ala Gln Val Asp Leu Cys Ala Thr Cys Thr Thr Gly Cys
                165                 170                 175

Leu Lys Gly Leu Ala Asn Val Lys Cys Ser Glu Leu Leu Lys Lys Trp
            180                 185                 190

Leu Pro Gly Arg Cys Ala Ser Phe Ala Asp Lys Ile Gln Lys Glu Val
        195                 200                 205

His Asn Ile Lys Gly Met Ala Gly Asp Arg
    210                 215
```

<210> SEQ ID NO 3
<211> LENGTH: 660
<212> TYPE: DNA
<213> ORGANISM: Metridia longa

<400> SEQUENCE: 3

```
atggatataa aggttgtctt tactcttgtt ttctcagcat tggttcaggc aaaatcaact      60
```

-continued

```
gaattcgatc ctaacattga cattgttggt ttagaaggaa aatttggtat aacaaacctt    120
gagacggatt tattcacaat atgggagaca atggaggtca tgatcaaagc agatattgca    180
gatactgata gagccagcaa ctttgttgca actgaaaccg atgctaaccg tggaaaaatg    240
cctggcaaaa aactgccact ggcagttatc atggaaatgg aagccaatgc tttcaaagct    300
ggctgcacca ggggatgcct tatctgtctt tcaaaaataa agtgtacagc caaaatgaag    360
gtgtacattc caggaagatg tcatgattat ggtggtgaca agaaaactgg acaggcagga    420
atagttggtg caattgttga cattcccgaa atctctggat ttaaggagat ggcacccatg    480
gaacagttca ttgctcaagt tgaacgttgc gcttcctgca ctactggatg tctcaaaggt    540
cttgccaatg ttaagtgctc tgaactcctg aagaaatggc tgcctgacag atgtgcaagt    600
tttgctgaca agattcaaaa agaagttcac aatatcaaag gcatggctgg agatcgttga   660
```

<210> SEQ ID NO 4
<211> LENGTH: 219
<212> TYPE: PRT
<213> ORGANISM: Metridia longa

<400> SEQUENCE: 4

```
Met Asp Ile Lys Val Val Phe Thr Leu Val Phe Ser Ala Leu Val Gln
 1               5                  10                  15

Ala Lys Ser Thr Glu Phe Asp Pro Asn Ile Asp Ile Val Gly Leu Glu
             20                  25                  30

Gly Lys Phe Gly Ile Thr Asn Leu Glu Thr Asp Leu Phe Thr Ile Trp
         35                  40                  45

Glu Thr Met Glu Val Met Ile Lys Ala Asp Ile Ala Asp Thr Asp Arg
     50                  55                  60

Ala Ser Asn Phe Val Ala Thr Glu Thr Asp Ala Asn Arg Gly Lys Met
 65                  70                  75                  80

Pro Gly Lys Lys Leu Pro Leu Ala Val Ile Met Glu Met Glu Ala Asn
                 85                  90                  95

Ala Phe Lys Ala Gly Cys Thr Arg Gly Cys Leu Ile Cys Leu Ser Lys
            100                 105                 110

Ile Lys Cys Thr Ala Lys Met Lys Val Tyr Ile Pro Gly Arg Cys His
        115                 120                 125

Asp Tyr Gly Gly Asp Lys Lys Thr Gly Gln Ala Gly Ile Val Gly Ala
    130                 135                 140

Ile Val Asp Ile Pro Glu Ile Ser Gly Phe Lys Glu Met Ala Pro Met
145                 150                 155                 160

Glu Gln Phe Ile Ala Gln Val Asp Arg Cys Ala Ser Cys Thr Thr Gly
                165                 170                 175

Cys Leu Lys Gly Leu Ala Asn Val Lys Cys Ser Glu Leu Leu Lys Lys
            180                 185                 190

Trp Leu Pro Asp Arg Cys Ala Ser Phe Ala Asp Lys Ile Gln Lys Glu
        195                 200                 205

Val His Asn Ile Lys Gly Met Ala Gly Asp Arg
    210                 215
```

<210> SEQ ID NO 5
<211> LENGTH: 573
<212> TYPE: DNA
<213> ORGANISM: Metridia longa

<400> SEQUENCE: 5

-continued

```
atgggagtca aacttatttt tgctgttgtt tgtgtcgcag ttgcccaggc tgccacaatt      60
caggaaaatt ttgaagacat tgatcttgta gccataggtg gcagctttgc atcagatgtt     120
gatgctaaca gaggtggaca tggtggacat cctggcaaaa agatgccaaa agaagtactt     180
atggaaatgg aagccaatgc taaacgagct ggctgccaca ggggttgtct ggtttgtctg     240
tcacacatca agtgcacagc acaaatgcag aagtttatcc caggaagatg ccatagttat     300
gcaggagaca aggattctgc tcaggagga attgccggtg gtgccattgt tgatatacct      360
gaaattgccg gatttaaaga aatgaagccc atggaacagt tcattgctca agttgatctc     420
tgtgaagatt gcacaactgg atgcctcaaa ggtcttgcca atgttcattg ctctgatctc     480
ctgaagaagt ggctgccatc aagatgtaag acatttgctt ccaaaattca atctcaagtg     540
gataccatca aaggtttggc tggagatcgt tga                                  573
```

<210> SEQ ID NO 6
<211> LENGTH: 190
<212> TYPE: PRT
<213> ORGANISM: Metridia longa

<400> SEQUENCE: 6

```
Met Gly Val Lys Leu Ile Phe Ala Val Val Cys Val Ala Val Ala Gln
1               5                   10                  15

Ala Ala Thr Ile Gln Glu Asn Phe Glu Asp Ile Asp Leu Val Ala Ile
            20                  25                  30

Gly Gly Ser Phe Ala Ser Asp Val Asp Ala Asn Arg Gly Gly His Gly
        35                  40                  45

Gly His Pro Gly Lys Lys Met Pro Lys Glu Val Leu Met Glu Met Glu
    50                  55                  60

Ala Asn Ala Lys Arg Ala Gly Cys His Arg Gly Cys Leu Val Cys Leu
65                  70                  75                  80

Ser His Ile Lys Cys Thr Ala Gln Met Gln Lys Phe Ile Pro Gly Arg
                85                  90                  95

Cys His Ser Tyr Ala Gly Asp Lys Asp Ser Ala Gln Gly Gly Ile Ala
            100                 105                 110

Gly Gly Ala Ile Val Asp Ile Pro Glu Ile Ala Gly Phe Lys Glu Met
        115                 120                 125

Lys Pro Met Glu Gln Phe Ile Ala Gln Val Asp Leu Cys Glu Asp Cys
    130                 135                 140

Thr Thr Gly Cys Leu Lys Gly Leu Ala Asn Val His Cys Ser Asp Leu
145                 150                 155                 160

Leu Lys Lys Trp Leu Pro Ser Arg Cys Lys Thr Phe Ala Ser Lys Ile
                165                 170                 175

Gln Ser Gln Val Asp Thr Ile Lys Gly Leu Ala Gly Asp Arg
            180                 185                 190
```

ISOLATED LUCIFERASES AND THE USE THEREOF

The invention relates to the nucleotide and amino acid sequences, and to the activity and use, of the luciferases LuAL, Lu164, Lu16, Lu39, Lu45, Lu52 and Lu22.

Luciferases

Luminescence is the term given to the emission of photons in the visible spectral range, with this emission being brought about by excited emitter molecules. In contrast to fluorescence, the energy for this is not supplied externally in the form of radiation of shorter wavelength.

A distinction is made between chemiluminescence and bioluminescence. Chemoluminescence is the term given to a chemical reaction which leads to an excited molecule which itself emits light when the excited electrons return to the normal energy level. Bioluminescence is the term used when this reaction is catalyzed by an enzyme. The enzymes which participate in the reaction are generally termed luciferases.

A review of luminescent organisms can be found in Hastings et al. 1995.

Luciferases are peroxidases or monooxygenases and dioxygenases. The enzyme substrates, which form the starting substances for the light-emitting products, are termed luciferins. They differ from species to species. The quantum yield of the systems lies between 0.1 and 0.9 photons per transformed substrate molecule (Idelgaufts, 1993).

Luciferases can be classified on the basis of their origin or their enzymic properties. An overview of some luciferase types is given below:

Bacterial Luciferase

TABLE 1

Bacterial luciferases

| Gene product | Organism | Substrate | λ | Expression | References/ Patents |
|---|---|---|---|---|---|
| Lux Genes | Vibrio fischerii | FMN, Dodecanal, NADH | 495 nm | cytosolic | Apley et al., 1985 Gustafson G., U.S. Pat. No. 5196524 |

Coelenterazine-Dependent Eukaryotic Luciferases

TABLE 2

Coelenterazine-dependent eukaryotic luciferases

| Gene product | Organism | Substrate | λ | Expression | References/ Patents |
|---|---|---|---|---|---|
| Renilla Luciferase | Renilla reniformis | Coelenterazine | 480 nm | cytosolic | Mathews et al., 1977 Lorenz et al, 1991 Lorenz et al. 1996 Alan, P; WO 0020619 Milton J., U.S. Pat. No. 5418155 Roelant C., WO 9938999 |
| Vargula/ Cypridia Luciferase | Vargula hilgendorferii | Vargula Luciferin | 460 nm | secretory | Thomspon et al., 1989 Thompson et al., 1990 Tora, JP 05064583 Tora, JP 08027200 Renard et al., WO 9520653 |
| Watasemia Luciferase | Watasemia scintillans | Watasemia Luciferin | ? | cytosolic | Inoue et al., 1976 |
| Olophorus Luciferase | Olophorus gracilirostris | Coelenterazine | 454 | secretion | Inouye et al, 2000 |
| Aequorin | Aequoria aequoria | Coelenterazine ($Ca^{2+}$ activated) | 470 nm | cytosolic | Head et al. 2000 Shimomura et al., 2000 Jones et al., 1999 Kendall et al., 1998 Inouye et al., 1985 Shimomura et al., 1969 Cormier et al., U.S. Pat. No. 5798441 Cormier et al., U.S. Pat. No. 5422266 |
| Obelin | Obelia | Coelenterazine | 470 nm | cytosolic | Matveev et al., 1999 Berestovskaya, 1999 |

Coelenterazine-Independent Eukaryotic Luciferase

TABLE 3

Coelenterazine-independent eukaryotic luciferases

| Gene product | Organism | Substrate | λ | Expression | References |
|---|---|---|---|---|---|
| Firefly Luciferase | *Photinus pyralis* | Firefly Luciferin, ATP | 550 nm | cytosolic | Webster et al., 1980<br>Gould et al., 1988<br>Sala-Newby et al, 1992<br>Bonin et al., 1994<br>Sherf B., U.S. Pat. No. 5670356<br>KIKK, JP 09187281 |

Luciferases can also be distinguished from each other on the basis of their substrate specificity. The most important substrates include coelenterazine (Jones et al., 1999) and luciferin, and also derivatives of the two substances. Diagrams of the substrates, and their transformation by luciferase, are shown below:

Luciferase Substrates

Some luciferase substrates, and their transformation, are depicted below by way of example. All the substrates which are shown here are transformed enzymically with the release of light and carbon dioxide ($CO_2$) and consumption of oxygen ($O_2$). The dependence of the reaction on cofactors or energy carriers (e.g. ATP in the case of Firefly Luciferase) is enzyme-specific.

Coelenterazine

Coelenteramide

Transformation of coelenterazine into coelenteramide by aequorin with the emission of light of wavelength 470 nm.

Luciferin

Oxyluciferin

Transformation of luciferin into oxyluciferin by Firefly Luciferase with the emission of light of wavelength 560 nm.

Vargula luciferin

Vargula oxyluciferin

Transformation of Vargula Luciferin into Vargula Oxyluciferin by Vargula Luciferase with the emission of light of wavelength 460 nm.

Reporter Systems

A reporter gene or indicator gene is the term which is generally given to genes whose gene products can readily be detected using simple biochemical or histochemical methods. At least 2 types of reporter gene are distinguished.
1. Resistance genes. Resistance genes is the term given to genes whose expression confers on a cell resistance to antibiotics or other substances whose presence in the growth medium leads to cell death when the resistance gene is absent.
2. Reporter gene. In recombinant DNA technology, the products of reporter genes are used as fused or unfused indicators. The most common reporter genes include beta-galactosidase (Alam et al., 1990), alkaline phosphatase (Yang et al., 1997; Cullen et al., 1992), luciferases and other photoproteins (Shinomura, 1985; Phillips G N, 1997; Snowdowne et al., 1984).

Classification of the Species Metridia longa
Arthropoda→→Crustacea→→Copepoda

The species *Metridia longa* belongs to the crustacea, especially the copepoda or zooplancton.

Isolating the cDNA

In order to investigate the bioluminescence activity of the species *Metridia longa*, specimens were caught in the White Sea (Kartesh Biological Station, Russia) and stored in liquid nitrogen. In order to prepare cDNA libraries of *Metridia longa*, the RNA was isolated by the method of Krieg (Krieg et al., 1996) using isothiocyanate. RT-PCR was carried out in order to prepare the cDNA. For this, 10 µg of RNA were incubated with reverse transcriptase (Superscript Gold II) in accordance with the following scheme:

| PCR | 1. | 30 seconds | 95° C. |
|---|---|---|---|
| | 2. | 6 minutes | 68° C. |
| | 3. | 10 seconds | 95° C. |
| | 4. | 6 minutes | 68° C. |

17 cycles of step 4 after step 3

In order to inactivate the polymerase, the reaction products were incubated with proteinase K at 37° C. for 30 minutes, and the cDNA was precipitated with ethanol. The cDNA was dissolved in water and incubated at 37° C. for one hour with SfiI. The reaction products were subjected to gel filtration in order to separate off small fragments. The fractionated cDNA was then ligated into the SfiI-cut and dephosphorylated λTriplEx2 vector. In order to prepare a λ phage expression library, the cloned cDNA fragments were subsequently packaged into λ phages using the SMART cDNA Library Construction Kit (Clontech) in-vitro packaging system.

The recombinant phages which contained a cDNA insertion with potential for expressing coelenterazine-dependent luciferases were identified by carrying out a library screening.

For this, bacterial lawns composed of *E. coli* XL1-Blue were plated out on 90 mm culture dishes and incubated at 37° C. for 10 hours. They were then infected with 2500 phages per culture dish, with this then being followed by an incubation phase of 8 hours at 37° C. to enable plaques to be formed. The culture dishes were subsequently stored at 4° C. for one hour in order to harden the soft agar.

In order to carry out a replica plating, nitrocellulose membranes were saturated with *E. coli* XL1-Blue suspensions and dried. The dry membranes were laid for 60 seconds on the phage plaques and then laid on fresh agar plates. The agar plates were then incubated at 37° C. for 2 hours and 4 ml of SOB medium (+10 mM MgSO4, 0.2% maltose) were added. The bacterial lawn was detached, resuspended in LB medium (+20 mM IPTG) and incubated at 37° C. for one hour. The bacteria were harvested by centrifugation and disrupted by ultrasonication, and the bioluminescence activity was determined in a luminometer after having added coelenterazine.

Culture plates giving a positive bioluminescence signal were divided into sectors and a fresh replica plating was carried out. The replica plating was continued until active individual plaques had been identified. In order to subclone the cDNA insertions in the phages in positive plaques [lacuna] took place into the pTriplEX2 vector in *E. coli* BM25.8 in accordance with the manufacturer's protocol for the SMART cDNA library construction kit. The pTriplEx2 cDNA-transfected *E. coli* were incubated overnight, at 37° C., in LB medium containing an ampicillin concentration of 100 µg/ml. In order to achieve overexpression, the overnight culture was diluted 1:150 with LB medium and incubated at 37° C. for 1 hour. Induction was then effected by adding IPTG (isopropylthiogalactoside) to a final concentration of 20 mM. The induced culture was incubated at 37° C. for 1 hour and the bacteria were harvested by centrifugation. The cells were disrupted by ultrasonication in 0.5 ml of SM buffer. The chemiluminescence was measured in a luminometer after adding 10 µl of coelenterazine ($10^{-4}$ M in methanol).

Three luciferases which exhibited coelenterazine-dependent luciferase activity were identified. The luciferases were designated Lu164, LuAL and Lu22. The luciferases are described in detail below.

The invention also relates to functional equivalents of the three luciferases. Functional equivalents are those luciferases which have a comparable substrate spectrum, which are secreted and which are at least 70% homologous. A homology of 80% or 90% is preferred. A homology of 95% is particularly preferred.

The luciferases are suitable for use as reporter genes for cellular systems, especially for receptors, for ion channels, for transporters, for transcription factors or for inducible systems.

The luciferases can be used in bacterial systems, for example for titer determination or as substrates for biochemical systems, especially for proteinases.

The luciferases can also be used as reporter enzymes which are coupled to antibodies or other proteins, e.g. for ELISA, for immunohistochemistry or for Western blotting.

The luciferases can be used in BRET (Bioluminescence Resonance Energy Transfer) systems.

The luciferases are also suitable for use as fusion proteins for confocal microscopy or for analyzing protein-protein interactions.

The luciferases can be used as reporter enzymes which are coupled to biotin, NHS, CN—Br or other coupling mediators, e.g. for ELISA or for immobilization.

The luciferases can furthermore be used as reporter enzymes which are coupled to DNA or RNA oligonucleotides, e.g. for Northern and Southern blotting or for real time PCR.

The invention also relates to the purification of the luciferases as wild-type or tag proteins, and to the use of the luciferases in in-vitro translation systems.

Nucleotide and Amino Acid Sequences

LuAL

The luciferase LuAL is a protein having a molecular weight of 23.7 kDa and an isoelectric point of 8.32. The coding nucleotide sequence is:

```
5' atggatatgagggttatctttgctcttgttttctcatcattggttca ggccaaatcaactgaattcgatcctaacattaacattgttggtttagaag gaaaatttggtataacaaaccttgagacggatttattcacaatatgggag acaatggatgtcatcaaatcagatattacagatactgatagagtcagcaa ctttgttcaactgaaaccgatgctaaccgtgggaaaatgcctggcaaaa aactgccactggcagttatcatggaaatgaagccaatgctttcaaagct ggctgcaccaggggatgccttatctgtctttcaaaaataaagtgtacagc caaaatgaaggtgtacattccaggaagatgtcatgattatggtggtgaca agaaaactggacaggcaggaatagttggtgcaattgttgacattcccgaa atctctggatttaaggagatggcacccatggaacagttcattgctcaagt tgatctttgcgctacctgcactactggatgtctcaaggtcttgccaatg ttaagtgctctgaactcctgaagaaatggctgcctggcagatgtgcaagt tttgctgacaagattcaaaaagaagttcacaatatcaaaggcatggctgg agatcgttga 3'
``` which gives rise to the following amino acid sequence:

MDMRVIFALVFSSLVQAKSTEFDPNINIVGLEGKFGITNLETDLFTIWET

MDVIKSDITDTDRVSNFVATETDANRGKMPGKKLPLAVIMEMEANAFKAG

CTRGCLICLSKIKCTAKMKVYIPGRCHDYGGDKKTGQAGIVGAIVDIPEI

SGFKEMAPMEQFIAQVDLCATCTTGCLKGLANVKCSELLKKWLPGRCASF

ADKIQKEVHNIKGMAGDR and the following amino acid composition:

| Ala: | 18 (8.3%) | Cys: | 10 (4.6%) | Asp: | 14 (6.4%) | Glu: | 12 (5.5%) |
|---|---|---|---|---|---|---|---|
| Phe: | 10 (4.6%) | Gly: | 19 (8.7%) | His: | 2 (0.9%) | Ile: | 18 (8.3%) |
| Lys: | 21 (9.6%) | Leu: | 15 (6.9%) | Met: | 10 (4.6%) | Asn: | 8 (3.7%) |
| Pro: | 7 (3.2%) | Gln: | 5 (2.3%) | Arg: | 7 (3.2%) | Ser: | 9 (4.1%) |
| Thr: | 15 (6.9%) | Val: | 14 (6.4%) | Trp: | 2 (0.9%) | Tyr: | 2 (0.9%) |

Lu164

Luciferase Lu164 is a protein having a molecular weight of 23.8 kDa and an isoelectric point of 7.81. The coding nucleotide sequence is:

```
5' atggatataaaggttgtctttactcttgttttctcagcattggttca ggcaaaatcaactgaattcgatcctaacattgacattgttggtttagaag gaaaatttggtataacaaaccttgagacggatttattcacaatatgggag acaatggaggtcatgatcaaagcagatattgcagatactgatagagccag caactttgttcaactgaaaccgatgctaaccgtgggaaaatgcctggca aaaaactgccactggcagttatcatggaaatggaagccaatgctttcaaa gctggctgcaccaggggatgccttatctgtctttcaaaaataaagtgtac agccaaaatgaaggtgtacattccaggaagatgtcatgattatggtggtg acaagaaaactggacaggcaggaatagttggtgcaattgttgacattccc gaaatctctggatttaaggagatggcacccatggaacagttcattgctca agttgaacgttgcgcttcctgcactactggatgtctcaaggtcttgcca atgttaagtgctctgaactcctgaagaaatggctgcctgacagatgtgca agttttgctgacaagattcaaaaagaagttcacaatatcaaaggcatggc tggagatcgttga 3
``` which gives rise to the following amino acid sequence:

MDIKVVFTLVFSALVQAKSTEFDPNIDIVGLEGKFGITNLETDLFTIWET

MEVMIKADIADTDRASNFVATETDANRGKMPGKKLPLAVIMEMEANAFKA

GCTRGCLICLSKIKCTAKMKVYIPGRCHDYGGDKKTGQAGIVGAIVDIPE

ISGFKEMAPMEQFIAQVDRCASCTTGCLKGLANVKCSELLKKWLPDRCAS

FADKIQKEVHNIKGMAGDR and the following amino acid composition:

| Ala: | 21 (9.6%) | Cys: | 10 (4.6%) | Asp: | 15 (6.8%) | Glu: | 13 (5.9%) |
|---|---|---|---|---|---|---|---|
| Phe: | 10 (4.6%) | Gly: | 18 (8.2%) | His: | 2 (0.9%) | Ile: | 18 (8.2%) |
| Lys: | 22 (10.0%) | Leu: | 14 (6.4%) | Met: | 10 (4.6%) | Asn: | 7 (3.2%) |
| Pro: | 7 (3.2%) | Gln: | 5 (2.3%) | Arg: | 7 (3.2%) | Ser: | 8 (3.7%) |
| Thr: | 14 (6.4%) | Val: | 14 (6.4%) | Trp: | 2 (0.9%) | Tyr: | 2 (0.9%) |

Lu22

Luciferase Lu22 is a protein having a molecular weight of 20.2 kDa and an isoelectric point of 7.89. The coding nucleotide sequence is:

```
5' atgggagtcaaacttattttgctgttgtttgtgtcgcagttgccca ggctgccacaattcaggaaaattttgaagacattgatcttgtagccatag gtggcagctttgcatcagatgttgatgctaacagaggtggacatggtgga catcctggcaaaaagatgccaaaagaagtacttatggaaatggaagccaa tgctaaacgagctggctgccacaggggttgtctggtttgtctgtcacaca tcaagtgcacagcacaaatgcagaagtttatcccaggaagatgccatagt tatgcaggagacaaggattctgctcagggaggaattgccggtggtgccat tgttgatatacctgaaattgccggatttaaagaaatgaagcccatggaac agttcattgctcaagttgatctctgtgaagattgcacaactggatgcctc aaaggtcttgccaatgttcattgctctgatctcctgaagaagtggctgcc atcaagatgtaagacatttgcttccaaaattcaatctcaagtggatacca tcaaaggttttggctggagatcgttga 3'
``` which gives rise to the following amino acid sequence:

MGVKLIFAVVCVAVAQAATIQENFEDIDLVAIGGSFASDVDANRGGHGGH

PGKKMPKEVLMEMEANAKRAGCHRGCLVCLSHIKCTAQMQKFIPGRCHSY

AGDKDSAQGGIAGGAIVDIPEIAGFKEMKPMEQFIAQVDLCEDCTTGCLK

GLANVHCSDLLKKWLPSRCKTFASKIQSQVDTIKGLAGDR and the following amino acid composition:

| Ala: | 21 (11.1%) | Cys: | 11 (5.8%) | Asp: | 12 (6.3%) | Glu: | 9 (4.7%) |
|---|---|---|---|---|---|---|---|
| Phe: | 7 (3.7%) | Gly: | 21 (11.1%) | His: | 6 (3.2%) | Ile: | 13 (6.8%) |
| Lys: | 16 (8.4%) | Leu: | 12 (6.3%) | Met: | 7 (3.7%) | Asn: | 4 (2.1%) |
| Pro: | 6 (3.2%) | Gln: | 9 (4.7%) | Arg: | 6 (3.2%) | Ser: | 9 (4.7%) |
| Thr: | 6 (3.2%) | Val: | 13 (6.8%) | Trp: | 1 (0.5%) | Tyr: | 1 (0.5%) |

These sequences are also given in the sequence listing.

Enzymic Activity and Biochemical Characterization of the Luciferases

The proteins LuAL, Lu164 and Lu22 are enzymes which release light while transforming coelenterazine. They therefore belong to the luciferases. The luciferases can be actively expressed in both bacterial and eukaryotic cells. The luciferases LuAl, Lu164 and Lu22 which are expressed in eukaryotic cells are secreted. No secretion takes place in connection with bacterial expression.

The activity of the luciferases is temperature-dependent. Temperature optima of 22° C. (for LuAL) and 27° C. (for Lu164) were determined for the luciferases LuAL and Lu164, respectively. The temperature optimum for luciferase Lu22 activity is 4° C. or lower.

EXAMPLES

Plasmids/Constructs

The vectors employed for preparing the constructs which are descibed below were the vectors pcDNA3.1(+) and pTriplEx2 from Clontech and the vector pASMplr (in-house construct possessing cAMP-sensitive promoter elements; cre). The derivatives of the vectors were designated pcDNA3-x, pTriplEx2-x and pASM-x.

LuAL

FIG. 1 shows the plasmid maps of the vectors pTriplEX2-LuAL, pcDNA3-LuAL and pASM-LuAL FIG. 2 shows the plasmid maps of the vectors pTriplEX2-Lu164, pcDNA3-Lu164 and pASM-Lu164

FIG. 3 shows the plasmid maps of the vectors pTriplEX2-Lu22, pcDNA3-Lu22 and pASM-Lu22

Coelenterazine Derivates as Substrates of Lu164

In order to identify substrates for Lu164, 10 µl solutions of different coelenterazine derivatives ($10^{-4}$M) were in each case incubated with 10 µl of supernatant from CHO-pcDNA3-Lu164 cell lines and the luminescence was measured. The coelenterazines were obtained from Molecular Probes (USA).

No differences as compared with luciferase Lu164 were seen in the case of luciferases LuAL and Lu22. Unmodified coelenterazine (FIG. B, coelenterazine a) was identified as being the optimal substrate for Lu164, LuAl and Lu22.

FIG. 4 shows coelenterazine derivatives as potential substrates for Lu164 and a graph of the measurement of luminescence for 30 seconds at 8.7 kV in a luminometer (RLU, relative light units); and also a diagram of the molecular structures of the coelenterazine derivatives.

Enzymic Activity of the Luciferases Lu164, LuAL and Lu22 in Dependence on Coelenterazine Bacterial Expression The bacterial expression took place in the E. coli strain BL21(DE3) as a result of transforming the bacteria with the expression plasmids pTriplEX2-Lu164, pTriplEX2-LuAL and pTriplEX2-Lu22. The transformed bacteria were incubated at 37° C. for 3 hours in LB medium and expression was induced for 4 hours by adding IPTG to a final concentration of 1 mM. The induced bacteria were harvested by centrifugation, resuspended in PBS and disrupted by ultrasonication. Coelenterazine ($10^{-4}$ M in methanol) or luciferin (Firefly Luciferin) was added to 5 µl of the lysate (5 mg/ml) and the chemiluminescence was measured.

The measurement, in RLU (relative light units), took place at 9.5 kV for 30 seconds. Values of 230 000, 320 000 and 260 000 RLU were measured in the case of Lu164, LuAL and Lu22, respectively. The enzymes were expressed in E. coli BL21(DE3) using the vectors pTriplEx2-Lu164, pTriplEx2-LuAL and pTriplEx2-Lu22.

Eukaryotic Expression

Constitutive eukaryotic expression was affected in CHO cells by transfecting the cells with the expression plasmids pcDNA3-Lu164, pcDNA3-LuAL and pcDNA3-Lu22 in transient experiments. For this, 10 000 cells in DMEM-F12 medium were plated, per well, in 96-well microtiter plates and incubated overnight at 37° C. The transfection was effected using the Fugene 6 kit (Roche) in accordance with the manufacturer's instructions. The transfected cells were incubated overnight at 37° C. in DMEM-F12 medium. The chemiluminescence in the medium (5 µl) and the cell lysate (5 µl) was measured for 30 seconds at 9.5 kV in a luminometer, at room temperature, after adding coelenterazine ($10^{-4}$ M in methanol).

Values of 680 000, 670 000 and 510 000 RLU (relative light units) were measured in the case of Lu164, LuAL and Lu22, respectively. The expression was effected in CHO cells using the vectors pcDNA3-Lu164, pcDNA3-LuAL and pcDNA3-Lu22.

Emission Spectra of the Luciferases Lu164, LuAL and Lu22

In order to measure the emission spectra, E. coli BL21 (DE3) cells were transformed with the plasmids pTriplEx2-Lu164, pTriplEx2-LuAL and pTriplEx2-Lu22 and overexpressed as described under 3.1. 50 µl of coelenterazine ($10^{-4}$ M) were added to 100 µl volumes of the bacterial lysates and the emission spectra were measured. Graphs of the emission spectra of the luciferases are shown below.

In the case of the luciferases LuAL, Lu164 and Lu22, maximum emission resulting from the substrate transformation takes place at a wavelength of about 490 nm.

FIG. 5 shows the emission spectra of the luciferases Lu164 (A), LuAL (B) and Lu22 (C) following bacterial expression (RLU, relative light units)

Secretion of the Luciferases Lu164, LuAL and Lu22 from CHO Cells, Taking as Examples Lu164 and LuAL In order to characterize the expression of the luciferases LuAL, Lu164 and Lu22 in eukaryotic cells, CHO cells were stably transfected with the plasmids pcDNA3-LuAl, pcDNA3-Lu164, pcDNA3-Fireluc and pcDNA3.1(+). The resulting clones were cultured in DMEM-F12 medium.

Firefly luciferase was used as a positive control for nonsecreted luciferase. The plasmid pcDNA3.1(+) was used as a control plasmid for detecting potential endogenous activity in the CHO parent cell.

In order to detect the secretion of the luciferases, 2000 cells were plated on 384-well microtiter plates. After 24 hours, the medium was removed and the cells were washed with Tyrode solution and 30 µl of fresh medium were added. The first measurement (0 h) then took place, in a luminometer at 9.5 kV for 30 seconds, after adding 5 µl of coelenterazine ($10^{-4}$ M) or luciferin in the case of the Firefly luciferase. The 1 h to 5 h measurements took place after one to five hours.

FIG. 6 depicts the increase in luciferase activity in the medium in dependence on the time. The Firefly luciferase was not secreted. The luciferases LuAL, Lu164 and Lu22 are secretory luciferases.

FIG. 6 shows the luciferase activity in the CHO cell medium (5 µl) after the CHO cells have been transfected with pcDNA3-LuAL, pcDNA3-Firefly, pcDNA3-Lu164 or pcDNA3 as the control vector without any cDNA insertion. (RLU, relative light units; h, hours; Firefly: Firefly luciferase)

Dependence of the Luciferase Activity on the Temperature

In order to determine the temperature dependence of the luciferases Lu22, Lu164 and LuAL, CHO cells were transiently transfected with the vectors pcDNA3-Lu22, pcDNA3-Lu164 and pcDNA3-LuAl and the luciferase activity in the supernatants was determined at temperatures of between 0 and 47° C. In order to do this, the cell supernatant and the coelenterazine solution were adapted to the measurement temperature for 5 minutes. The measurement took place at 9.5 kV for 30 seconds in a luminometer.

FIG. 7 shows the luminescence which was measured, in dependence on the temperature, in the case of the luciferases LuAl, Lu164 and Lu22. The temperature optimum for the luciferase activity of LuAL is 27° C. A temperature optimum of 22° C. and of 4° C. or lower was determined in the case of Lu164 and Lu22, respectively.

FIG. 7 shows the temperature-dependent luciferase activity in CHO cell medium (5 µl) following transfection with pcDNA3-LuAL, pcDNA3-Firefly and pcDNA3-Lu164. (RLU: relative light units; medium: DMEM-F12+10% FCS)

Induced Expression of the Luciferases Lu164, LuAL and Lu22 in CHO Cells Taking as an Example LuAL Eukaryotic expression was induced in CHO cells by transfecting the cells with the expression plasmid pASM-LuAL in transient experiments. For this, 10 000 cells in DMEM-F12 medium were plated per well in 96-well microtiter plates and incubated overnight at 37° C. The transfection was effected using the Fugene 6 kit (Roche) in accordance with the manufacturer's instructions. The transfected cells were incubated overnight, at 37° C., in DMEM-F12 medium. They were then induced with Forkolin ($10^{-5}$ M) for 5 hours. The chemiluminescence in the medium and in the cell lysate was then measured, at 9.5 kV for 30 seconds, in a luminometer after having added coelenterazine ($10^{-4}$ M in methanol).

FIG. 8 shows the induced expression of LuAL in CHO cells. The expression was induced for 5 hours with Forskolin ($10^{-5}$ M) at 37° C. The activity was measured in 10 µl of cell supernatant (RLU: relative light units; induction factor: ratio of induced RLU to uninduced RLU)

Use of the Luciferases Lu164, LuAL and Lu22 as Reporter Genes in Cellular Systems Taking as Examples the Receptors NPY2 and A2A and using LuAL as the Reporter Gene In order to be able to analyze the activation of G protein-coupled receptors by receptor-specific ligand in cell-based systems, the cDNA sequence for luciferase LuAL was cloned into the expression vector pASMplr. The expression vector pASMplr contains cAMP-sensitive promoter elements (CRE) which enable the intracellular concentration of cAMP to be measured indirectly. The luciferase serves as the reporter gene in the system.

The use of the luciferases Lu22, Lu164 and Lu22 as reporter genes in cellular systems was demonstrated by taking as an example the G protein-coupled receptors NPY2 (neuropeptide receptor 2) and A2A (adenosine receptor 2a). To do this, the stable clone CHO-pASM-LuAL was transiently transfected with the vector pcDNA3-NPY2 or the vector pcDNA3-A2A. The receptor NPY2 is a Gi-coupled receptor, while the A2A receptor is a Gs-coupled receptor.

The A2A receptor was activated for 4 h by adding 1 µM NECA. The NPY2 receptor was activated by adding 10 µM NPY2 peptide in the presence of $10^{-5}$ M Forskolin. The luciferase activity in the medium (30 µl) was measured, at 9.5 kV and for 30 seconds in a luminometer, after having added coelenterazine ($10^{-4}$ M).

FIG. 9 shows the use of the luciferases as reporter genes for cellular systems taking as an example the G protein-coupled receptors A2A and NPY2. (RLU: relative light units)

REFERENCES/PATENTS

Apley E C, Wagner R, Engelbrecht S., Rapid procedure for the preparation of ferredoxin-NADP+oxidoreductase in molecularly pure form at 36 kDa., Anal Biochem. 1985 October; 150(1):145-54.

Berestovskaya N G, Shaloiko L A, Gorokhovatsky A Y, Bondar V S, Vysotski E S, Maximov J E, von Doehren H, Alakhov Y B. Cotranslational formation of active photoprotein obelin in a cell-free translation system: direct ultrahigh sensitive measure of the translation course. Anal Biochem. 1999 Mar. 1;268(1):72-8.

Bonin et al. Photinus pyralis luciferase. Gene. 1994 141: 75-77

Alam J, Cook J L. Reporter genes: application to the study of mammalian gene transcription. Anal Biochem. 1990 Aug. 1; 188(2):245-54

Cullen Bryan R., Malim Michael H., Secreted placental alkaline phosphatase as a eukaryotic reporter gene. Methods in Enzymology. 216:362ff Hastings, Cell Physiology: Source book, Sperelakis N. (ed.), Academic press, pp 665-681, 1995

Head J F, Inouye S, Teranishi K, Shimomura O., The crystal structure of the photoprotein aequorin at 2.3 A resolution. Nature. 2000 May 18;405(6784):372-6.

Gould S., Suresh S., Firefly luciferase as a tool in molecular an dcell biology. Anal. Biochem. 1988, 161:501-507

Idelgaufts H., Gentechnologie von A-Z [Recombinant DNA Technology from A-Z]. VCH Verlag, Weinheim, 1993

Inouye S, Noguchi M, Sakaki Y, Takagi Y, Miyata T, Iwanaga S, Miyata T, Tsuji F I. Cloning and sequence analysis of cDNA for the luminescent protein aequorin. Proc Natl Acad Sci USA 1985 May; 82(10):3154-8

Inouye, S., Kakoi, H., Goto, T., Tetrahedron Lett., 34, 2971-2974 (1976)

Inouye, S., Watanebe, H., Nakamura, H. and Shimomura, O., FEBS letters 481 (2000) 19-25

Jones Keith, Hibbert Frank, Keenan Martine. Glowing jellyfish, luminescence and a molecule called coelenterazine. *Tibtech.* 1999. 17: 477ff Kendall Jonathan M., Badminton Michael N. Aequoria victoria bioluminescence moves into an exciting new era. *Tibtech.* 1998 16:216

Krieg, S., Castles, C., Allred, D., Benedix, M., Fuqua S., RNA from air-dried frozen sections for RT-PCR and differential display. *Biotechniques.* 1996 September; 21(3):425-8.

Lorenz W W, McCann R O, Longiaru M, Cormier M J., Isolation and expression of a cDNA encoding *Renilla reniformis* luciferase. *Proc Natl Acad Sci USA.* 1991 May 15;88(10):4438-42.

Lorenz W W, Cormier M J, O'Kane D J, Hua D, Escher A A, Szalay A A., Expression of the Renilla reniformis luciferase gene in mammalian cells. *J Biolumin Chemilumin.* 1996 January-February; 11(1):31-7.

Mathews J. C. et al. Purification and propeties of remilla reniformis luciferase. *Biochemistry.* 1977, 16(1): 85-91

Matveev S V, Lewis J C, Daunert S., Genetically engineered obelin as a bioluminescent label in an assay for a peptide. *Anal Biochem.* 1999 May 15;270(1):69-74.

Phillips G N. Structure and dynamics of green fluorescent protein. *Curr Opin Struct Biol.* 1997 December; 7(6): 821-7

Sala-Newby et al., Expression of recombinant firefly luciferase. *Biochem Soc. Transact.* 1992, 20:143S Shimomura O, Johnson F H., Properties of the bioluminescent protein aequorin. *Biochemistry.* 1969 October; 8(10): 3991-7.

Shimomura O., Bioluminescence in the sea: photoprotein systems. *Symp Soc Exp Biol.* 1985;39:351-72.

Shimomura O, Teranishi K., Light-emitters involved in the luminescence of coelenterazine. *Luminescence.* 2000 January-February; 15(1):51-8.

Snowdowne K W, Borle A B. Measurement of cytosolic free calcium in mammalian cells with aequorin. *Am J Physiol.* 1984 November; 247(5 Pt 1):C396-408.

Thompson E M, Nagata S, Tsuji F I., Cloning and expression of cDNA for the luciferase from the marine ostracod *Vargula hilgendorfii. Proc Natl Acad Sci USA.* 1989 September; 86(17):6567-71.

Thompson E M, Nagata S, Tsuji F I., *Vargula hilgendorfii* luciferase: a secreted reporter enzyme for monitoring gene expression in mammalian cells. *Gene.* 1990 Dec. 15;96(2):257-62.

Ungrin M D, Singh L M, Stocco R, Sas D E, Abramovitz M., An automated aequorin luminescence-based functional calcium assay for G-protein-coupled receptors. *Anal Biochem.* 1999 Jul. 15;272(1):34-42.

Webster J J, Chang J C, Manley E R, Spivey H O, Leach F R., Buffer effects on ATP analysis by firefly luciferase. *Anal Biochem.* 1980 Jul. 15; 106(1):7-11.

Yang Te-Tuan, Sinai Parisa, Kitts Paul A. Kain Seven R., Quantification of gene expresssion with a secreted alkaline phosphatase reporter system. *Biotechnique.* 1997 23(6) 1110ff JP 05064583, *Tora*, (TORAY IND Inc.), Luciferase modified with antigen, antibody, hapten or hormone, etc.—is isolated from *Vargula hilgendorfii*, useful in bio-luminescent analysis JP 08027200, *Tora*, (TORAY IND Inc.), Protein comprising luciferase fused to IgG binding domain—useful as diagnostic reagent in chemiluminescent immunoassays JP 09187281, Kikk, (KIKKOMAN Corp.), Antibody-firefly luciferase fused protein —and related products i.e. firefly luciferase fused gene, recombinant DNA and its preparation U.S. Pat. No. 5,196,524, Gustafson G.; Ingolia T; Kirchner G.; Roberts J., (Lilly & Co), Recombinant DNA encoding fusion protein with bacterial luciferase activity—comprises coding regions of lux A and B genes isolated from specific naturally bio luminescent bacteria, and DNA linker of specified restriction enzyme recognition site U.S. Pat. No. 5,418,155, Milton J, Cornier; William W. Lorenz, Isolated *Renilla Luciferase* and Method of use thereof U.S. Pat. No. 5,422,266, Cormier M J; Prasher D., (UNIV GEORGIA RES FOUND INC), DNA coding for apo: aequorin—useful for recombinant prodn. of apo:aequorin which is a bio:luminescent marker in chemical and biochemical assays U.S. Pat. No. 5,670,356, Sherf B.; Wood K (Promega Corp), Modified firefly luciferase gene—encoding cytoplasmic form of luciferase enzyme U.S. Pat. No. 5,798,441 Cormier M J.; Prasher D., (UNIV GEORGIA RES FOUND INC), New isolated apoaquorin polypeptide—useful as a luminescent marker in bio/chemical assays WO 0020619, Alan P.; Liu Jingxue, Secreted *renilla luciferase*

WO 9520653, Renard J P; Thompson E. M; Thompson E, (INRA INST NAT RECH AGRONOMIQUE), Detecting transgenic embryos using *Vargula luciferase* gene as a marker—allows identification of such embryos at the blastocyst stage, also transgenic animals, embryos and cell line contg. this gene WO 9938999, Roelant C. (Packard Instr. Co. Inc.), Detecting the presence of *renilla luciferase* in a sample by detecting luminescence of the sample

The invention claimed is:

1. An isolated nucleic acid molecule selected from the group consisting of
    (a) a nucleic acid molecule comprising SEQ ID NO: 3;
    (b) a nucleic acid molecule which exhibits at least 90% sequence identity to the nucleic acid molecule of SEQ ID NO: 3, and wherein said nucleic acid molecule encodes luciferase.

2. The nucleic acid molecule of claim 1, wherein the sequence contains a functional promoter located 5' to the coding strand of the sequence.

3. An expression vector comprising the nucleic acid molecule according to claim 2.

4. A transformed host cell comprising the vector of claim 3.

* * * * *